(12) United States Patent
Motai et al.

(10) Patent No.: US 10,786,240 B2
(45) Date of Patent: Sep. 29, 2020

(54) METHOD OF DELIVERING AND RECOVERING CURVED NEEDLE

(71) Applicant: OLYMPUS CORPORATION, Tokyo (JP)

(72) Inventors: Kosuke Motai, Hidaka (JP); Shotaro Takemoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 205 days.

(21) Appl. No.: 16/050,824

(22) Filed: Jul. 31, 2018

(65) Prior Publication Data

US 2020/0038011 A1 Feb. 6, 2020

(51) Int. Cl.
  *A61B 17/04* (2006.01)
  *A61B 17/06* (2006.01)
  *A61B 17/062* (2006.01)

(52) U.S. Cl.
  CPC ...... *A61B 17/0469* (2013.01); *A61B 17/0482* (2013.01); *A61B 17/062* (2013.01); *A61B 17/06066* (2013.01); *A61B 2017/0608* (2013.01)

(58) Field of Classification Search
  CPC ....... A61B 17/04; A61B 17/06; A61B 17/062; A61B 17/0469; A61B 17/0482; A61B 17/06066; A61B 2017/0608
  See application file for complete search history.

(56) References Cited

U.S. PATENT DOCUMENTS 5,197,979 A * 3/1993 Quintero ............... A61F 2/2427
  623/1.26
6,478,791 B1 * 11/2002 Carter ................. A61B 17/062
  606/1

FOREIGN PATENT DOCUMENTS

JP 2003-284722 A 10/2003

* cited by examiner

*Primary Examiner* — Vi X Nguyen
(74) *Attorney, Agent, or Firm* — Oliff PLC

(57) ABSTRACT

A method of delivering and recovering a curved needle includes a step of inserting a first needle holder into abdominal cavity, a step of inserting a second needle holder holding a curved needle into gastrointestinal tract, a step of penetrating gastrointestinal wall with the curved needle to protrude the curved needle to the abdominal cavity, a step of removing the curved needle from the gastrointestinal wall and delivering the curved needle and the suture thread to the abdominal cavity, a suture step of suturing tissues in the abdominal cavity, a step of protruding the curved needle to the gastrointestinal tract, a step of removing the curved needle from the gastrointestinal wall and returning the curved needle from the abdominal cavity to the gastrointestinal tract, and a step of taking out the curved needle from the gastrointestinal tract to outside of body to recover the curved needle.

10 Claims, 8 Drawing Sheets

METHOD OF DELIVERING AND RECOVERING CURVED NEEDLE

TECHNICAL FIELD

The present invention relates to a method of delivering a curved needle into and recovering the curved needle from abdominal cavity of a patient.

BACKGROUND ART

Nowadays, a laparoscopic surgery with respect to various organs as treatment targets is employed. Generally, in the laparoscopic surgery, a hole is made on the abdominal wall and a trocar is disposed into the hole. Further, a laparoscope and various treatment tools are introduced into the abdominal cavity via the trocar.

The laparoscopic surgery is minimally invasive compared with a laparotomy surgery, however, method of achieving more minimally invasive is studied. A method of using a thinner trocar is proposed, however, a curved needle used for suturing cannot pass through if the trocar is too thin.

In Japanese Unexamined Patent Application, First Publication No. 2003-284722, an anastomotic device configured to be introduced into the gastrointestinal tract for an anastomosis of the stomach and the jejunum is disclosed.

SUMMARY OF INVENTION

The present invention relates to a method of delivering and recovering a curved needle.

This method has a step of inserting a first needle holder into abdominal cavity via a hole made on abdominal wall, a step of inserting a second needle holder holding a curved needle with a suture thread into gastrointestinal tract via natural orifice, a step of penetrating gastrointestinal wall with the curved needle held by the second needle holder from the gastrointestinal tract toward the abdominal cavity to protrude part of the curved needle to the abdominal cavity, a step of removing the curved needle and the suture thread from the gastrointestinal wall and delivering the curved needle and the suture thread to the abdominal cavity by holding and pulling the part of the curved needle protruded to the abdominal cavity by the first needle holder, a suture step of suturing tissues using the curved needle held by the first needle holder, a step of sticking the curved needle into the gastrointestinal wall from the abdominal cavity toward the gastrointestinal tract to protrude part of the curved needle to the gastrointestinal tract after the suture step, a step of removing the curved needle and the suture thread connected to the curved needle from the gastrointestinal wall and returning the curved needle from the abdominal cavity to the gastrointestinal tract by holding and pulling the part of the curved needle protruded to the gastrointestinal tract by the second needle holder, and a step of taking out the curved needle from the gastrointestinal tract to outside of body via the natural orifice to recover the curved needle while keeping a state of holding the curved needle by the second needle holder.

DESCRIPTION OF EMBODIMENT

An embodiment of the present invention will be described by referring to FIG. 1 to FIG. 9.

A method of delivering and recovering a curved needle according to the present embodiment is employed by at least two surgeons including a first surgeon in charge of procedures in the abdominal cavity and a second surgeon in charge of procedures in the gastrointestinal tract. Other assistance such as a laparoscope scopist and the like may be added besides the two surgeons.

Figure 1:
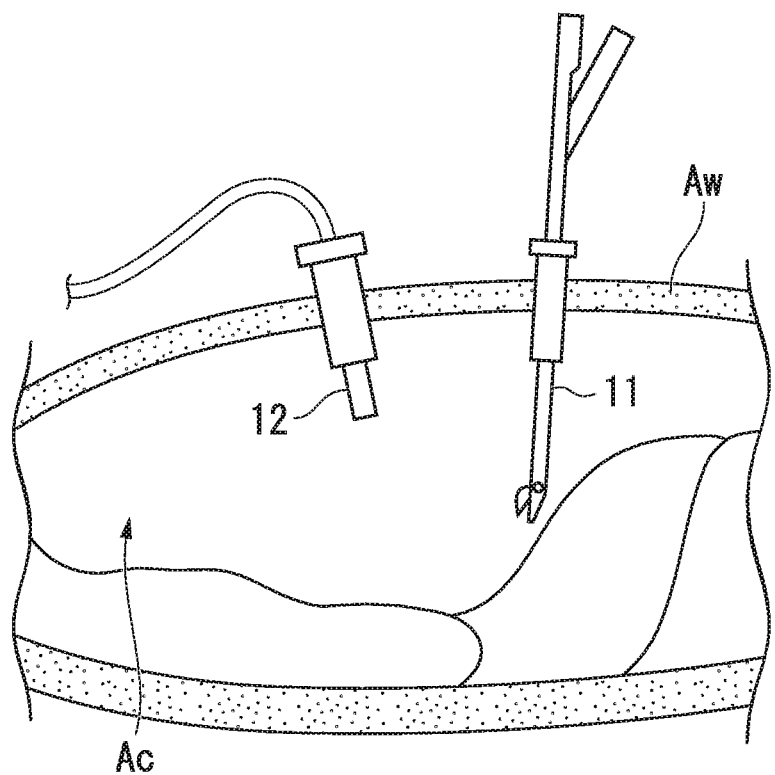
FIG. 1 is a view showing a step A of a method of delivering and recovering a curved needle according to an embodiment of the present invention.

The first surgeon forms a hole at the abdominal wall Aw and inserts a needle holder (first needle holder) 11 into the hole to introduce a laparoscope 12 and the first needle holder 11 into the abdominal cavity Ac, as shown in FIG. 1 (Step A). A trocar may be disposed at the hole made at the abdominal wall Aw and the first needle holder 11 may be introduced into the abdominal cavity Ac via the trocar.

Figure 2:
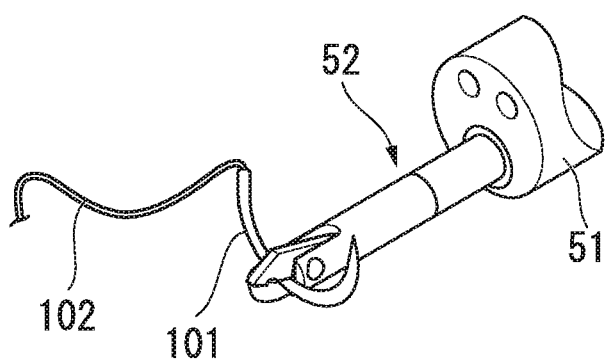
FIG. 2 is a view showing a state of protruding a distal end of a second needle holder from a distal opening of a flexible endoscope to hold a curved needle.
Figure 3:
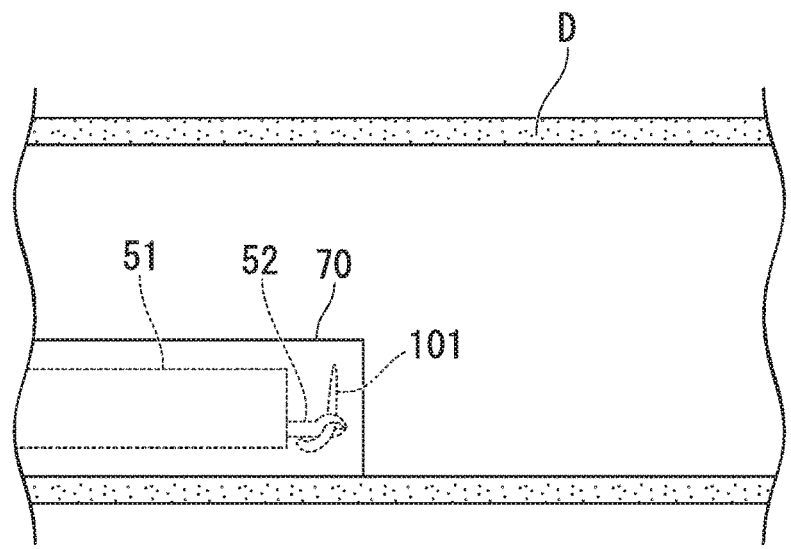
FIG. 3 is a view showing a step B of the method of delivering and recovering a curved needle.
Figure 4:
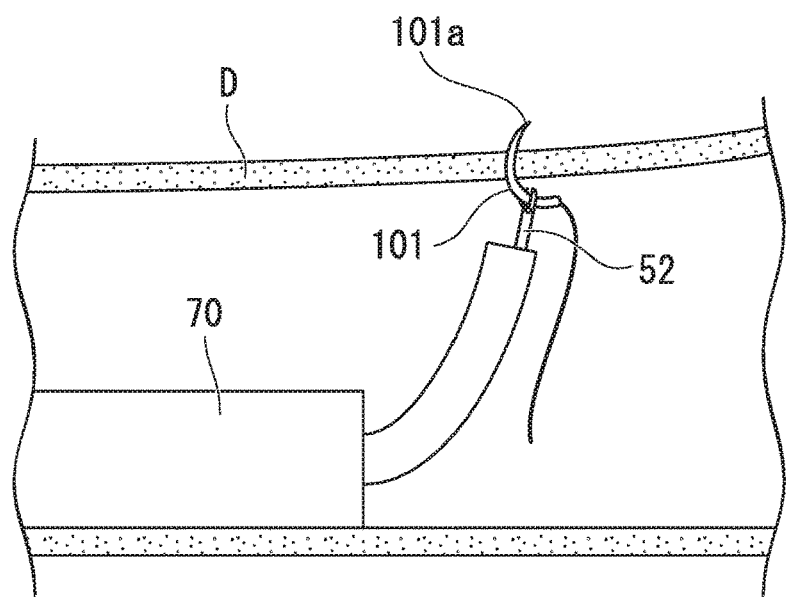
FIG. 4 is a view showing a step C of the method of delivering and recovering a curved needle.

The second surgeon inserts a flexible needle holder (second needle holder) 52 from a forceps port of a flexible endoscope 51 and protrudes a distal end portion of the second needle holder 52 from a distal opening of the flexible endoscope 51, as shown in FIG. 2. Further, a curved needle 101 with a suture thread 102 is held by a holding portion of the second needle holder 52 protruded from the distal opening, and the flexible endoscope 51 and the second needle holder 52 are inserted into an overtube 70 (see FIG. 3).

The second surgeon inserts the overtube 70 into the gastrointestinal tract of a patient from natural orifice such as mouth, anus, and the like, and moves a distal end portion of the overtube 70 and the curved needle 101 held by the second needle holder 52 to the vicinity of a target site of the laparoscopic surgery (Step B). At this time, the curved needle 101 held by the second needle holder 52 is configured to maintain the flexible endoscope 51 at a position not to protrude from a distal end of the overtube 70 such that the curved needle 101 can be prevented from coming contact with the gastrointestinal tract D.

The first surgeon confirms a position of the distal end portion of the overtube 70 in the gastrointestinal tract by the laparoscope 12. Methods shown as follows can be given as examples of a method of the confirmation.

confirming based on illumination light by the flexile endoscope 51 requesting the second surgeon to press the gastrointestinal wall using the overtube 70 for finding a deformed portion In the case of confirming based on the illumination light by the flexible endoscope 51, since the illumination light by the laparoscope 12 is brighter than the illumination light by the flexible endoscope 51 generally, the illumination light by the laparoscope 12 may be adjusted to be dark so as to find the illumination light by the flexible endoscope 51 easily.

Other methods such as attaching ink and the like to the gastrointestinal tract for marking, and using marking device such as a magnet and the like may be adopted.

The first surgeon confirms the position of the distal end portion of the overtube 70 and takes the position of the distal end portion of the overtube, positions of organs in the vicinity thereof, and distributions of the blood vessels and nerves into consideration to determine a transfer position of the curved needle 101 at the gastrointestinal tract D and inform the second surgeon with the transfer position. Methods shown as follows can be given as examples of a method of informing the second surgeon with the transfer position.

using the first needle holder 11 and the laparoscope 12 to press the transfer position so as to deform an inner wall of the gastrointestinal tract D into a convex shape moving the illumination of the distal end portion of the laparoscope 12 to approach the transfer position and intensely illuminating the transfer position by the laparoscope 12

Other methods such as the method of marking by ink, and using marking device may be adopted.

The second surgeon confirms the transfer position and protrudes the flexible endoscope 51 and the distal end portion of the second needle holder 52 from the overtube 70. Subsequently, shown as FIG. 4, the second surgeon operates the flexible endoscope 51 to penetrate a wall of the gastrointestinal tract D (gastrointestinal wall) with the curved needle 101 held by the second needle holder 52 from the gastrointestinal tract toward the abdominal cavity and protrudes a distal end of the curved needle 101a to the outside of the gastrointestinal tract D, that is, into the abdominal cavity (Step C).

Figure 5:
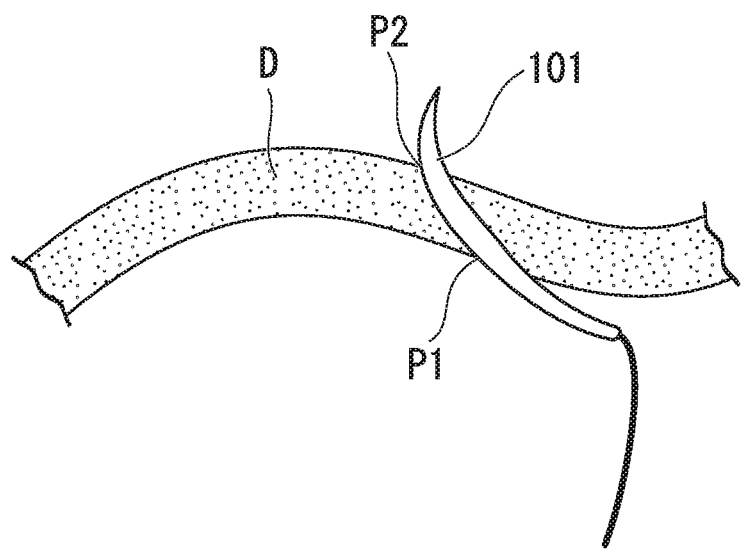
FIG. 5 is a view showing a state of the curved needle in the gastrointestinal wall.

The Step C is employed while observing the inside of the gastrointestinal tract D such that the curved needle 101 is stuck into the gastrointestinal wall while being kept in an observation view-field of the flexible endoscope 51. At this time, since the postoperative care is easy, as shown in FIG. 5, it is prefer that the distal end of the curved needle 101 which is stuck into the gastrointestinal wall is moved inside the gastrointestinal wall in a direction along a wall surface to cause a sticking position P1 and a position P2 protruded to the abdominal cavity to be different with each other in at least one of a longitudinal direction and a circumferential direction of the gastrointestinal tract D.

Figure 6:
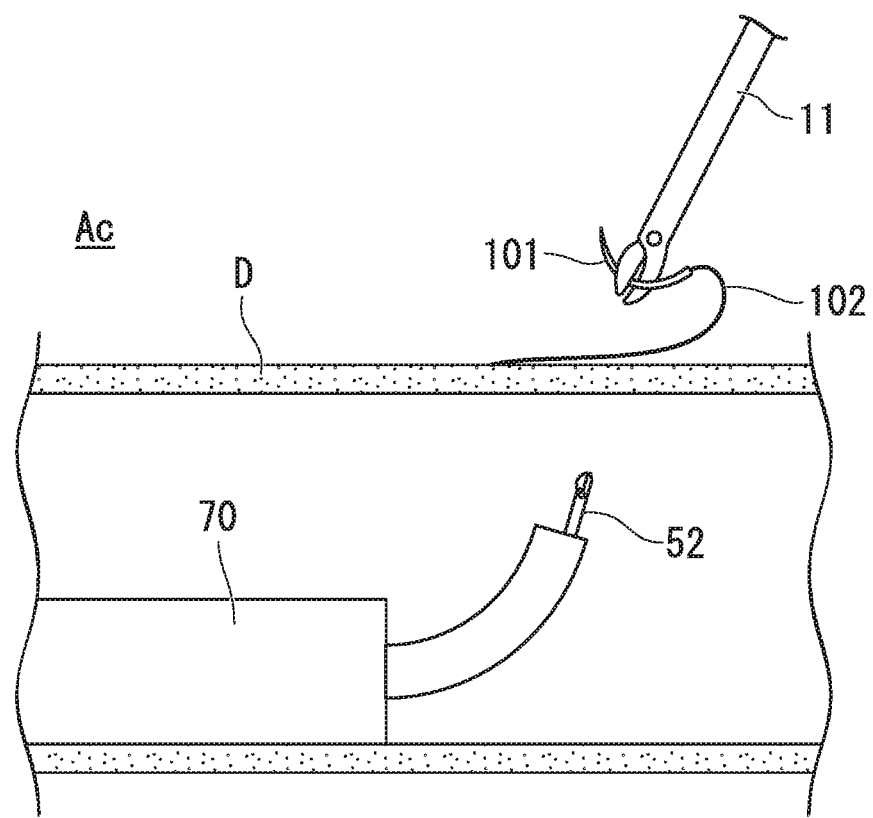
FIG. 6 is a view showing a step D of the method of delivering and recovering a curved needle.

The first surgeon holds the curved needle 101 protruded to the abdominal cavity by the first needle holder 11 and the second surgeon relaxes the holding by the second needle holder 52. Accordingly, the curved needle 101 and the suture thread 102 are transferred from the second 52 needle holder to the first needle holder 11. When the first surgeon removes the curved needle 101 and the suture thread 102 from the gastrointestinal wall by the first needle holder 11, as shown in FIG. 6, both of the curved needle 101 and the suture thread 102 are delivered from the gastrointestinal tract D to the abdominal cavity Ac (Step D). The first surgeon moves the curved needle 101 and the suture thread 102 being held toward suturing target tissues in the abdominal cavity.

The first surgeon uses the curved needle and the suture thread to suture the suturing target tissues (suture step). The suturing target tissues varies including various luminal organs, details will be described later, in this embodiment, an example of suturing a hole formed in the peritoneum during a hernia sac excision will be described.

Figure 7:
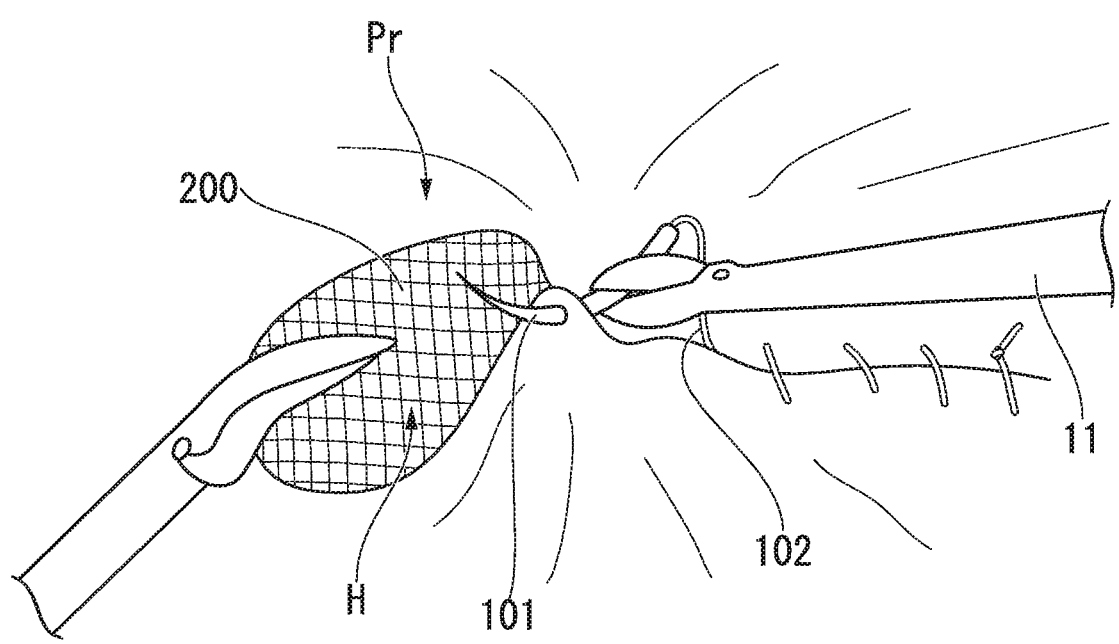
FIG. 7 is a view showing an example of intraperitoneal suture as a suture step of the method of delivering and recovering a curved needle.

The first surgeon removes the hernia sac and covers a hole formed in the muscular layer with a mesh 200. Thereafter, as shown in FIG. 7, the first surgeon uses the curved needle 101 and the suture thread to suture a hole H formed in the peritoneum Pr so as to reduce the hole H.

When the desired suture is finished, the first surgeon cuts the suture thread 102 to separate the curved needle 101 from the sutured tissues and returns the curved needle 101 to the gastrointestinal tract D. Firstly, the first surgeon informs the second surgeon with a position where the curved needle 101 is stuck into the gastrointestinal wall. Communication of the sticking position can be employed in the same way as the communication of the transfer position, however, it is noted that the curved needle 101 is held by the second needle holder 11.

Figure 8:
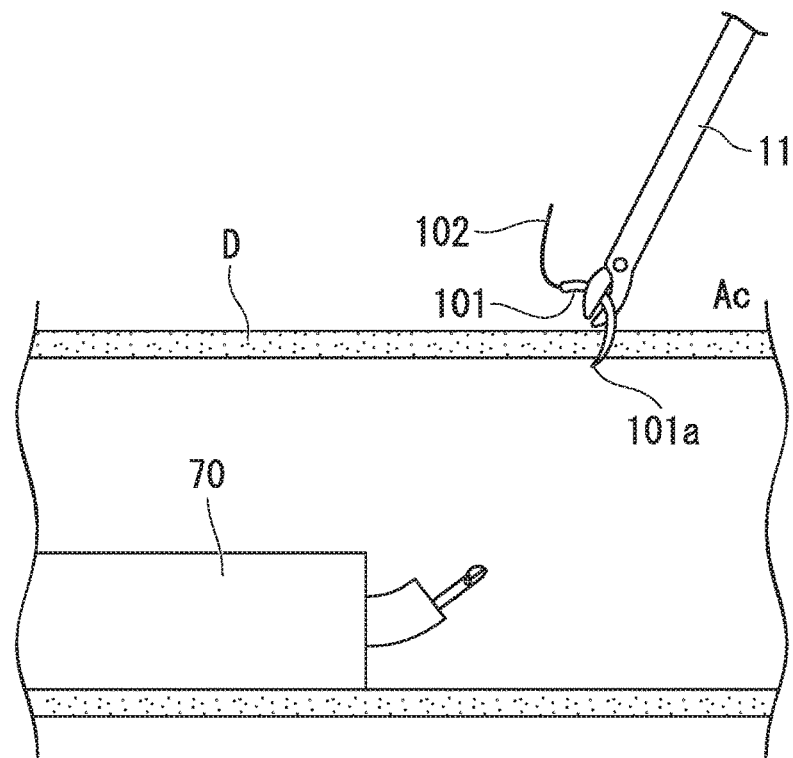
FIG. 8 is a view showing a step E of the method of delivering and recovering a curved needle.

After the second surgeon confirms the sticking position, as shown in FIG. 8, the first surgeon penetrates the gastrointestinal wall with the curved needle 101 held by the first needle holder 11 from the abdominal cavity Ac toward the gastrointestinal tract D to protrude the distal end 101a of the curved needle 101 to the gastrointestinal tract D (Step E). In the Step E, the second surgeon recognizes a position where the curved needle 101 protrudes to the gastrointestinal tract by capturing the sticking position by the first surgeon in the observation view field of the flexible endoscope 51 from the inside of the gastrointestinal tract D. Then, in the state in which the position where the curved needle 101 protrudes to the gastrointestinal tract is captured in the observation view field of the flexible endoscope 51, the first surgeon sticks the curved needle 101 into the gastrointestinal tract D to protrude part of the curved needle 101 to the gastrointestinal tract. At this time, in the same way as the Step C, the curved needle 101 which is stuck into the gastrointestinal wall may be moved inside the wall to make the curved needle 101 to be protruded at a different position from the sticking position. That is, the curved needle 101 may be obliquely stuck into the gastrointestinal wall so as to make the curved needle 101 to be protruded at a position displaced from the sticking position.

Figure 9:
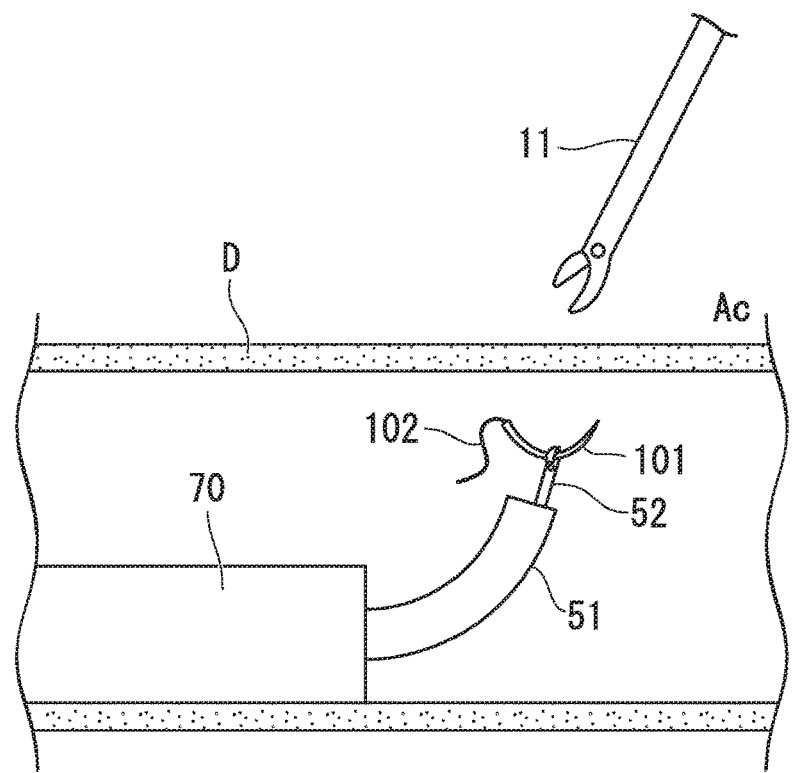
FIG. 9 is a view showing a step F of the method of delivering and recovering a curved needle.

When the second surgeon holds the curved needle 101 protruded to the gastrointestinal tract D by the second needle holder 52 and the first surgeon relaxes the holding by the first needle holder 11, the curved needle is transferred from the first needle holder 11 to the second needle holder 52. When the second surgeon uses the second needle holder 52 to remove the curved needle 101 from the gastrointestinal wall, as shown in FIG. 9, both of the curved needle 101 and the suture thread 102 are delivered from the abdominal cavity Ac into the gastrointestinal tract D (Step F). The second surgeon retracts the flexible endoscope 51 and the second needle holder 52 with respect to the overtube 70 to move the curved needle 101 into the overtube 70. The overtube 70, the flexible endoscope 51, and the second needle holder 52 are removed to the outside of the body to recover the curved needle 101 (Step G).

The method of delivering and recovering a curved needle according to the present embodiment is finished.

As described above, in the method of delivering and recovering a curved needle according to the present embodiment, the curved needle 101 is delivered into the abdominal cavity by being introduced into the gastrointestinal tract via the natural orifice, being stuck into the gastrointestinal wall and protruded to the abdominal cavity, and being received by the first needle holder in the abdominal cavity. Accordingly, the curved needle 101 can be delivered into the abdominal cavity without passing through the abdominal wall. As a result, different from the anastomotic device disclosed in Japanese Unexamined Patent Application, First Publication No. 2003-284722, it is possible to suture tissues apart from the gastrointestinal tract where the curved needle 101 is received.

Generally, a curved needle has a circular arc shape and a minimum length of a chord of the circular arc shape is substantially 8 millimeters. Accordingly, a trocar having an inner diameter of substantially 10 millimeters is necessary for delivering the curved needle into the abdominal cavity through the abdominal wall. Thus, in a laparoscope surgery together with suture procedures, it is necessary to enlarge at least one hole among the holes formed on the abdominal wall so as to make the curved needle can pass through the hole, and there is a limitation to reduce the invasion with respect to the patient.

When the method of delivering and recovering a curved needle according to the present embodiment is applied to the laparoscope surgery, it is not necessary to take the matter of passing the curved needle through the trocar and the hole formed on the abdominal wall into consideration, thus it is possible to achieve the goal of reducing the invasion to the patient at a higher level. For example, it is possible to form a hole with a diameter of substantially 3 millimeters on the abdominal wall and directly insert a small-diameter laparoscope and treatment tools through the hole to employ procedures without installing a trocar.

Various modifications can made to the method of delivering a curved needle according to the present embodiment. Hereinafter, several modifications will be described as examples, however, these modifications are not limited thereto and other modifications are possible. Also, two or more than two modifications may be suitably combined.

Before moving the curved needle 101 into the gastrointestinal tract D, the overtube 70 may be placed in the gastrointestinal tract D in advance by using the flexible endoscope 51 and the overtube 70 only.

Since complicated suture is not employed in the gastrointestinal tract D and the curved needle 101 only has to be stuck into the gastrointestinal wall, a general grasping forceps may be adopted as the second needle holder.

Either of introducing the first needle holder 11 into the abdominal cavity or introducing the second needle holder 52 into the gastrointestinal tract may be employed at first, and introducing the first needle holder 11 into the abdominal cavity and introducing the second needle holder 52 into the gastrointestinal tract may be employed parallelly.

Before the Step C, if necessary, the first surgeon may move the organs and tissues in the vicinity of the gastrointestinal tract to secure a region for making the curved needle 101 protrude to the abdominal cavity safely.

In the suture step, to secure a space inside the abdominal cavity, a gas suction may be employed in the gastrointestinal tract for narrowing the gastrointestinal tract. In other words, when the suture procedures are employed in the abdominal cavity, a broad space in the abdominal cavity can be secured by employing the gas suction in the gastrointestinal tract.

When the curved needle is stuck in the gastrointestinal tract, gas may be supplied into the gastrointestinal tract for widening the gastrointestinal tract. In this case, a tension is imparted to the gastrointestinal wall so as to make the puncture be easy or prevent the curved needle from sticking a wall facing the wall where the curved needle is stuck from the abdominal cavity side to the gastrointestinal tract.

Next, several examples of procedures to which the method of delivering and recovering a curved needle according to the present embodiment can be suitably applied will be described.

(Sleeve Gastrectomy)

A Sleeve Gastrectomy is a surgical procedure of reducing a volume of the stomach by surgical removal of a portion of the stomach at the Greater Curvature side so as to make the stomach into a thin shape as a banana. In a case where the method of delivering and recovering a curved needle according to the present embodiment is applied to this surgical procedure, it just needs to introduce the flexible endoscope 51 and the second needle holder 52 into the stomach and stick the curved needle 101 in the stomach wall so as to protrude the curved needle 101 to the abdominal cavity.

Figure 10:
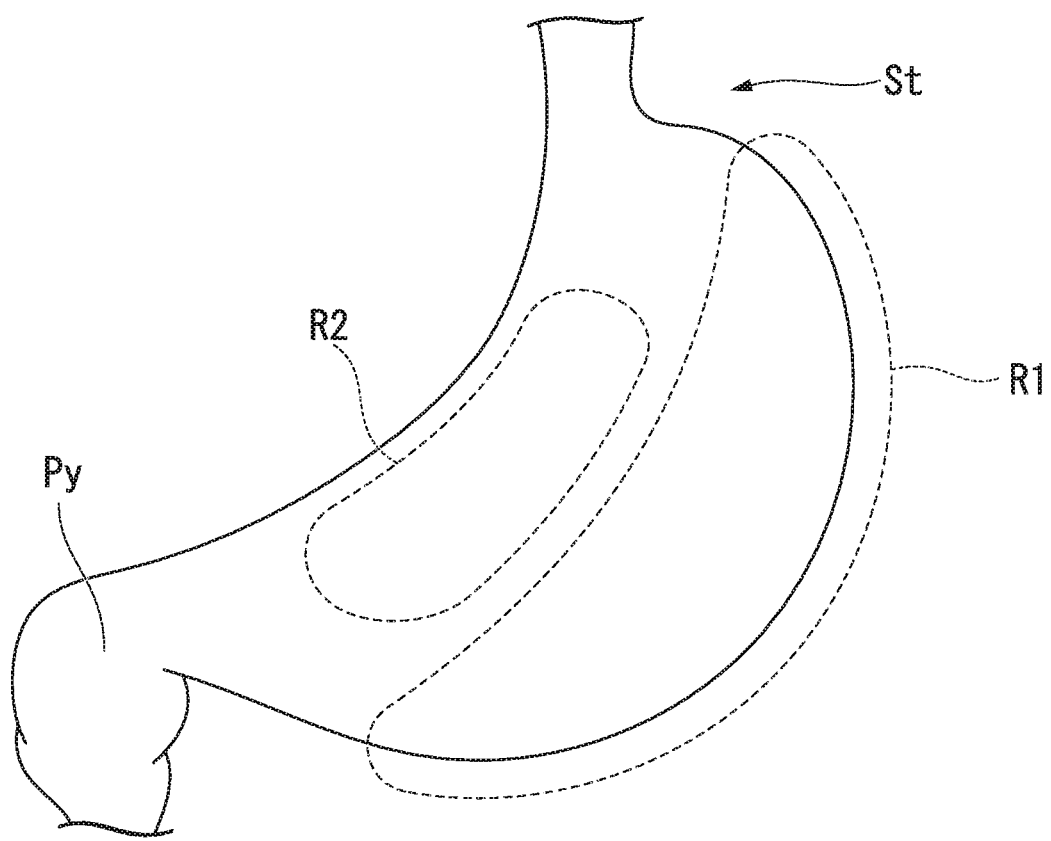
FIG. 10 is a view showing an application of delivering and recovering a curved needle with respect to Sleeve Gastrectomy.

In the Sleeve Gastrectomy, as shown in FIG. 10, it is preferable to transfer the curved needle from the inside of the Stomach St toward the abdominal cavity at a dissection region R1 since there is no damage to the remaining tissues after the procedure. Since it is easy to confirm the protruded curved needle 101 using the laparoscope 12, it is preferable to use a portion at an anterior wall side of the stomach in the dissection region R1. When the curved needle 101 is protruded at the anterior wall side, there is an advantage that a possibility that the curved needle 101 comes in contact with the gastro-epiploic artery becomes lower and also a possibility that the curved needle 101 collides with organs surrounding the stomach St becomes lower.

In the Sleeve Gastrectomy, it is possible to reinforce a staple line formed during the dissection using the curved needle delivered into the abdominal cavity.

It is preferable to transfer the curved needle 101 from the inside of the abdominal cavity toward the inside of the stomach St at the anterior wall side of the remaining stomach corpus (region R2 shown in FIG. 10) after the dissection. Since a wall at the region R2 is thinner than that of the pyloric Py, it is easy to stick the curved needle 101 during the transfer. Further, a possibility that the curved needle 101 collides with the surrounding organs is low.

(Roux-en-Y Gastric Bypass)

Figure 11:
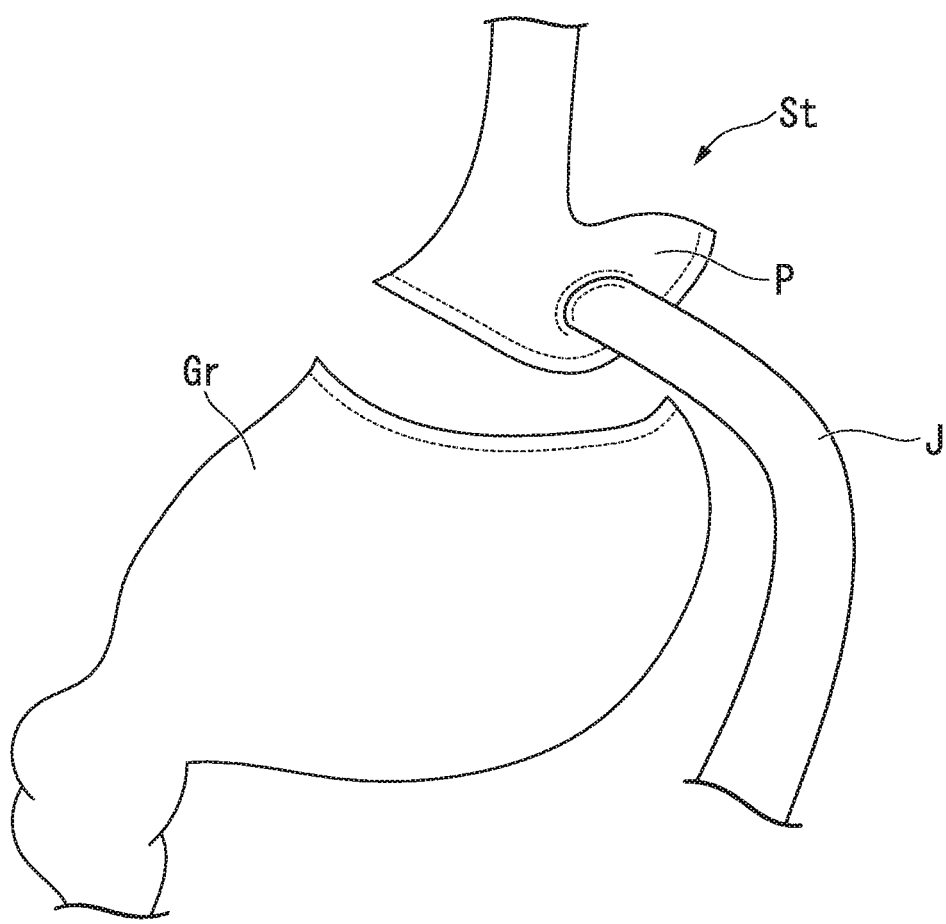
FIG. 11 is a view showing an application of delivering and recovering a curved needle with respect to Roux-en-Y Gastric Bypass.

As shown in FIG. 11, a Roux-en-Y Gastric Bypass is a surgical procedure of dividing the stomach St into a pouch P having a small volume and a remaining stomach Gr and anastomosing the pouch P with the jejunum J. In a case of applying the method of delivering and recovering a curved needle according to the present embodiment to this surgical procedure, it just needs to introduce the second needle holder 52 into the stomach and stick the curved needle 101 in the stomach wall so as to protrude the curved needle 101 to the abdominal cavity.

Similar to the Sleeve Gastrectomy, it is preferable to transfer the curved needle 101 from the inside of the stomach St toward the abdominal cavity at the anterior wall side of the stomach. In a case where the curved needle 101 is transferred before dividing the stomach St, the curved needle 101 may be transferred at either of the pouch P or the remaining stomach Gr. In a case where the curved needle 101 is transferred after dividing the stomach St, the curved needle 101 is transferred at the pouch P.

In the Roux-en-Y Gastric Bypass, it is possible to reinforce staple lines formed at the pouch P and the remaining stomach Gr during the dividing of the stomach St, deploy the anastomosis of the pouch P and the jejunum J, or reinforce a staple line formed at the anastomosis region of the pouch P and the jejunum J.

It is preferable to transfer the curved needle 101 from the inside of the abdominal cavity toward the inside of the stomach St at the anterior wall side of the pouch P.

(Colectomy)

Figure 12:
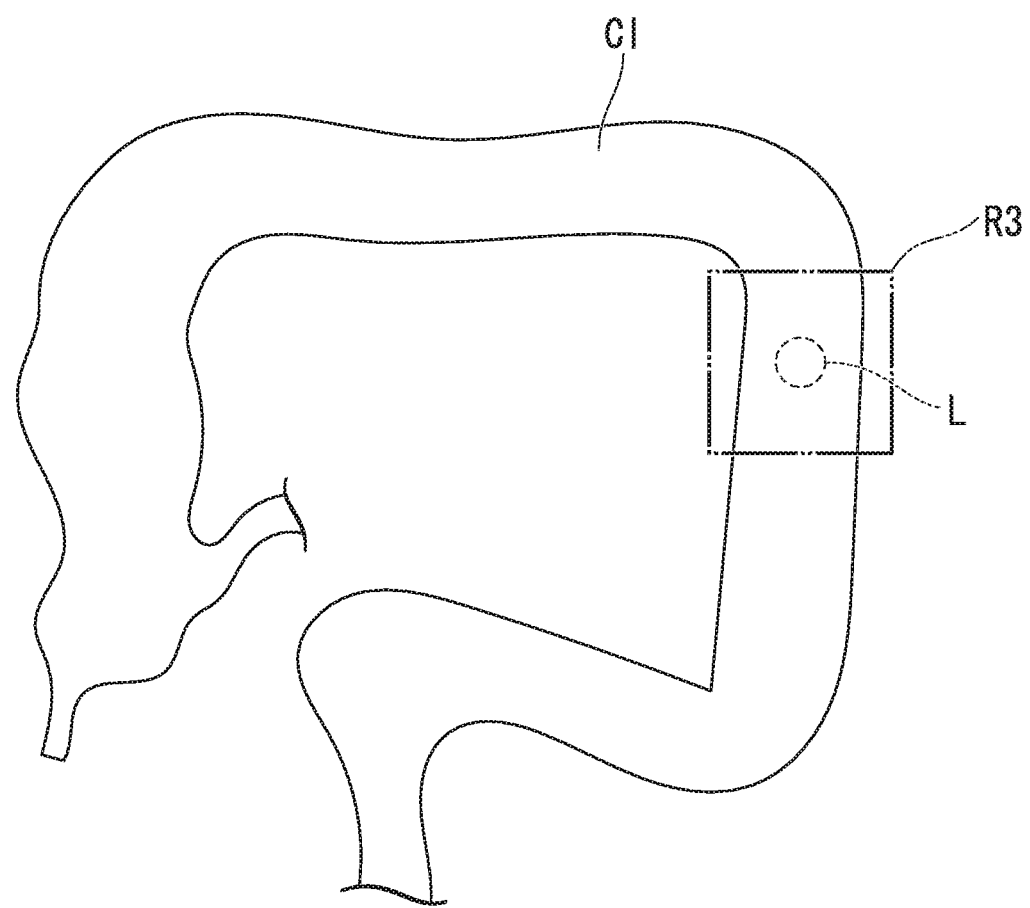
FIG. 12 is a view showing an application of delivering and recovering a curved needle with respect to Colectomy.

The method of delivering and recovering a curved needle according to the present embodiment can also be applied to a Colectomy of dissecting a region R3 (see FIG. 12) of the colon Cl where a dissection target lesion L such as a polyp or a tumor, and the like is positioned, and deploying an anastomosis of the remaining parts of the colon. In this case, it just needs to introduce the flexible endoscope 51 and the second needle holder 52 from the anus into the inside of the colon Cl and stick the curved needle 101 in a wall of the colon Cl so as to protrude the curved needle 101 to the abdominal cavity.

Generally, there is no problem to transfer the curved needle 101 from the inside of the colon Cl toward the abdominal cavity in a portion of the colon outside of the pelvis, however, it is preferable to transfer the curved needle 101 in a portion apart from the dissection target lesion L by a predetermined distance or more than the predetermined distance and closer to the anus. When the curved needle 101 is transferred in such a portion, a possibility that the curved needle 101 comes in contact with the dissection target lesion L is low, and the dissection target lesion L does not come in contact with the overtube 70 or the flexible endoscope 51. Further, an insertion amount of the overtube 70 or the flexile endoscope 51 is reduced so as to deploy the procedure easily.

It is preferable to transfer the curved needle 101 from the inside of the abdominal cavity toward the colon Cl in a portion closer to the anus than an anastomosis portion after the suture procedure.

In the Colectomy, it is possible to reinforce the colon anastomosis portion using the curved needle 101 delivered into the abdominal cavity.

(Procedures by Cooperating Laparoscope and Endoscope)

The method of delivering and recovering a curved needle can also be applied to procedures deployed by cooperating a laparoscope and an endoscope such as a Laparoscopy and Endoscopy Cooperative Surgery (LSCS) or a Non-exposed Endoscopic Wall-inversion Surgery (NEWS), and the like.

In a case where a hole is formed at the gastrointestinal tract during the procedure, the curved needle 101 can be delivered into the abdominal cavity from the hole formed at the gastrointestinal tract during the procedure. In a case where the gastrointestinal tract is dissected by using a stapler and the like without forming a hole at the gastrointestinal tract, similar to the embodiment described above, the curved needle can be delivered and recovered between the gastrointestinal tract and the abdominal cavity by sticking the curved needle 101 to the gastrointestinal wall.

The method of delivering and recovering a curved needle according to the present embodiment can be applied to a uterine myomectomy. In this case, defect closure after the uterine myomectomy can be deployed using the delivered curved needle.

Tissues in living body to which the method of delivering and recovering a curved needle according to the present embodiment is applied may be mesentery. In this case, the suture step includes a procedure of suturing a mesentery with another mesentery.

Tissues in living body to which the method of delivering and recovering a curved needle according to the present embodiment is applied may be greater omentum. In this case, the suture step includes a procedure of suturing the greater omentum with a luminal organ.

An embodiment and several application examples of the present invention have been described above, however, technical scope of the present invention is not limited to the embodiment and the application examples. Additions, omissions, substitutions and other changes in the structure are possible without departing from the spirit of the present invention.

The invention claimed is:

1. A method of delivering and recovering a curved needle, comprising:
    a step of inserting a first needle holder into abdominal cavity via a hole made on abdominal wall;
    a step of inserting a second needle holder holding a curved needle with a suture thread into gastrointestinal tract via natural orifice;
    a step of penetrating gastrointestinal wall with the curved needle held by the second needle holder from the gastrointestinal tract toward the abdominal cavity to protrude part of the curved needle to the abdominal cavity;
    a step of removing the curved needle and the suture thread from the gastrointestinal wall and delivering the curved needle and the suture thread to the abdominal cavity by holding and pulling the part of the curved needle protruded to the abdominal cavity by the first needle holder;
    a suture step of suturing tissues using the curved needle held by the first needle holder;
    a step of sticking the curved needle into the gastrointestinal wall from the abdominal cavity toward the gastrointestinal tract to protrude part of the curved needle to the gastrointestinal tract after the suture step;
    a step of removing the curved needle and the suture thread connected to the curved needle from the gastrointestinal wall and returning the curved needle from the abdominal cavity to the gastrointestinal tract by holding and pulling the part of the curved needle protruded to the gastrointestinal tract by the second needle holder; and
    a step of taking out the curved needle from the gastrointestinal tract to outside of body via the natural orifice to recover the curved needle while keeping a state of holding the curved needle by the second needle holder.

2. The method of delivering and recovering a curved needle according to claim 1, wherein the gastrointestinal tract is stomach, and the curved needle is stuck into part of an anterior wall of the stomach.

3. The method of delivering and recovering a curved needle according to claim 1, wherein a position at which the curved needle is stuck into the gastrointestinal wall from the inside of the gastrointestinal tract and a position at which the curved needle protrudes from the gastrointestinal wall toward the inside of the abdominal cavity are different with each other in at least one of a longitudinal direction and a circumferential direction of the gastrointestinal tract.

4. The method of delivering and recovering a curved needle according to claim 1, wherein the suture thread is cut inside the abdominal cavity after the suture step.

5. The method of delivering and recovering a curved needle according to claim 1, wherein gas inside the gastrointestinal tract is sucked during the suture step.

6. The method of delivering and recovering a curved needle according to claim 1, wherein gas is supplied into the gastrointestinal tract when the curved needle is stuck in the gastrointestinal wall.

7. The method of delivering and recovering a curved needle according to claim 1, wherein luminal organs are sutured in the suture step.

8. The method of delivering and recovering a curved needle according to claim 1, wherein a mesentery is sutured with another mesentery in the suture step.

9. The method of delivering and recovering a curved needle according to claim 1, wherein greater omentum and a luminal organ are sutured with each other in the suture step.

10. The method of delivering and recovering a curved needle according to claim 1, further comprising a step of inserting an endoscope into the gastrointestinal tract via natural orifice before the step of protruding part of the curved needle to the inside of the gastrointestinal tract,
    wherein the step of protruding part of the curved needle to the inside of the gastrointestinal tract includes protruding part of the curved needle from the gastrointestinal wall in a field of view of the endoscope inserted into the gastrointestinal tract.

\* \* \* \* \*